United States Patent [19]

Phillips et al.

[11] 4,299,221

[45] Nov. 10, 1981

[54] IRRIGATION AND SUCTION HANDPIECE

[75] Inventors: Earl G. Phillips, Kalamazoo Township, Kalamazoo County; Robert W. Insalaco, Portage, both of Mich.

[73] Assignee: Stryker Corporation, Kalamazoo, Mich.

[21] Appl. No.: 79,870

[22] Filed: Sep. 28, 1979

[51] Int. Cl.$^3$ .......................... A61M 1/00; A61C 1/02

[52] U.S. Cl. ....................................... 128/276; 433/100

[58] Field of Search ............................ 433/99, 100, 98; 128/240, 241, 276, 277, 278; 15/320, 321; 285/33, 304, 320

[56] References Cited

U.S. PATENT DOCUMENTS

| | | | |
|---|---|---|---|
| 747,493 | 12/1903 | Scruggs | 285/320 |
| 2,449,497 | 9/1948 | McLeod | 128/276 |
| 2,985,469 | 5/1961 | Bowman, Jr. | 285/304 |
| 3,065,749 | 11/1962 | Brass | 128/276 |
| 3,208,145 | 9/1965 | Turner | 128/276 |
| 3,469,582 | 9/1969 | Jackson | 128/276 |
| 3,568,318 | 3/1971 | Martin | 433/100 |
| 3,610,242 | 10/1971 | Sheridan | 128/276 |
| 3,749,090 | 7/1973 | Stewart | 128/276 |
| 3,889,675 | 6/1975 | Stewart | 128/240 |
| 3,964,484 | 6/1976 | Reynolds et al. | 128/276 |
| 3,986,262 | 10/1976 | Casillas | 32/22 |
| 4,049,000 | 9/1977 | Williams | 128/276 |
| 4,075,761 | 2/1978 | Behne et al. | 32/27 |
| 4,182,038 | 1/1980 | Fleer | 433/85 |

*Primary Examiner*—Lee S. Cohen

*Assistant Examiner*—J. L. Kruter

*Attorney, Agent, or Firm*—Blanchard, Flynn, Thiel, Boutell & Tanis

[57] ABSTRACT

An irrigation-suction handpiece assembly, for dental and surgical use at an operating site, includes a handle containing longitudinally extending, side-by-side suction and irrigant passageways respectively connectible to a source of subatmospheric pressure (i.e., a vacuum source) and an irrigant fluid source. An irrigant valve is actuable for alternately opening and blocking flow of irrigant from the irrigant source through the irrigant passageway. An air pressure conduit includes a third passageway in the handle and connectible to an air pressure source which is not atmospheric pressure and not influenced by pressure changes in the suction passageway. This air pressure source is either a further subatmospheric pressure source or a compressed gas source. The third passageway has a relief opening in the handle selectively openable or closable by the hand of the operator for effecting a change in the pressure within the third passageway. The irrigant valve has a control input coupled with the air pressure conduit and third passageway and responsive to such change in air pressure therein for shifting between its open and blocking states to thereby control the flow of irrigant fluid to the operating site.

5 Claims, 7 Drawing Figures

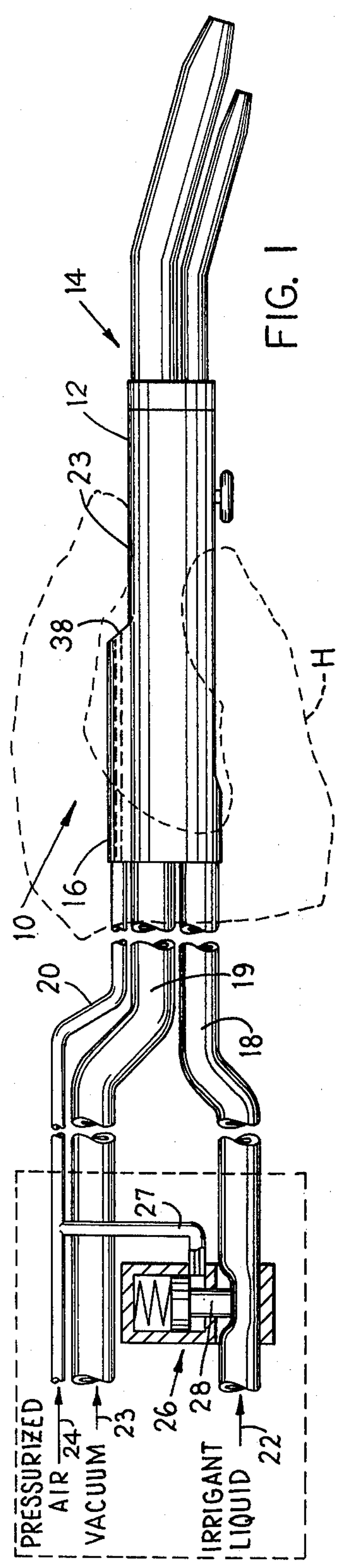
FIG. 1
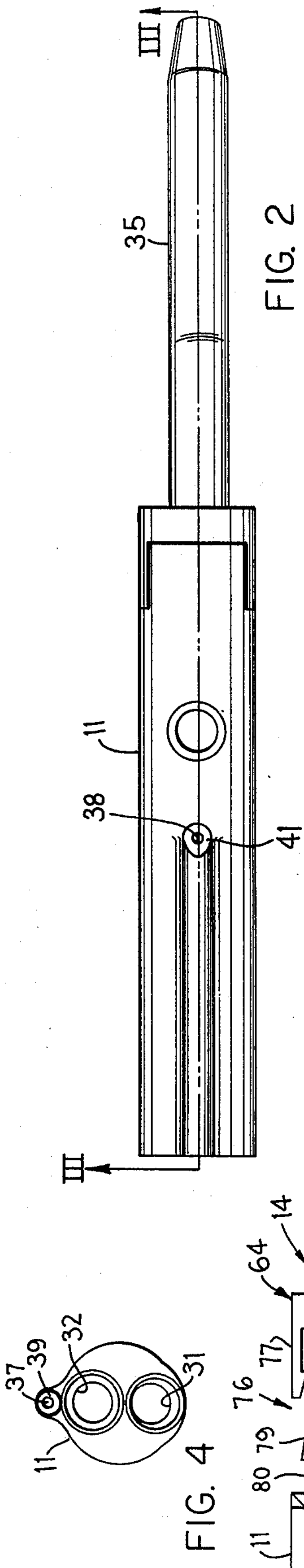
FIG. 2
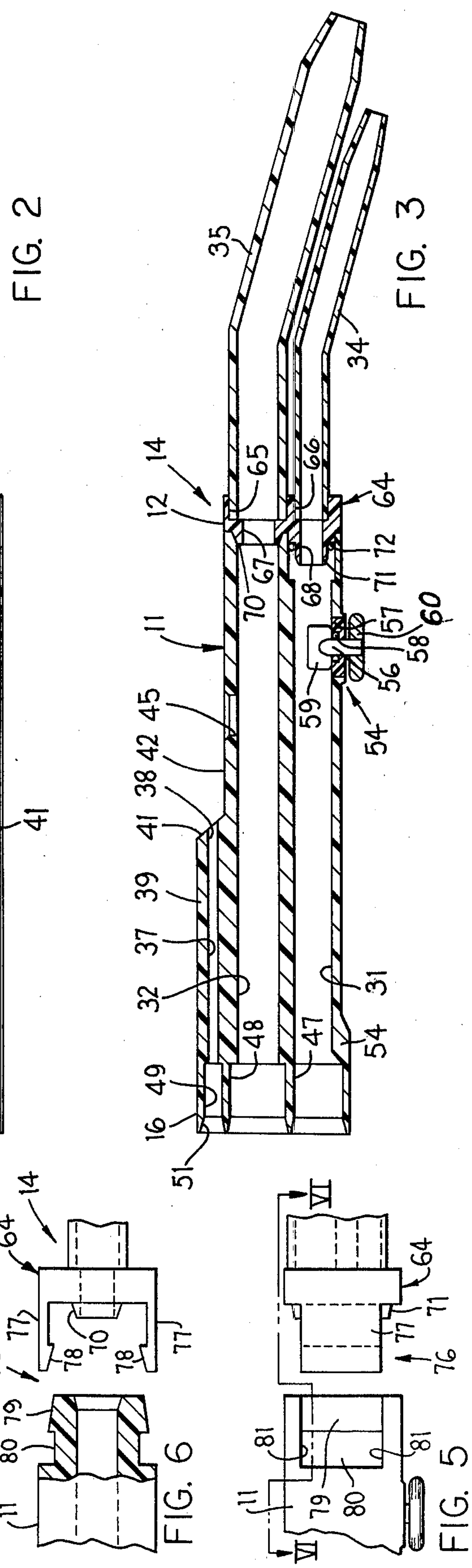
FIG. 3
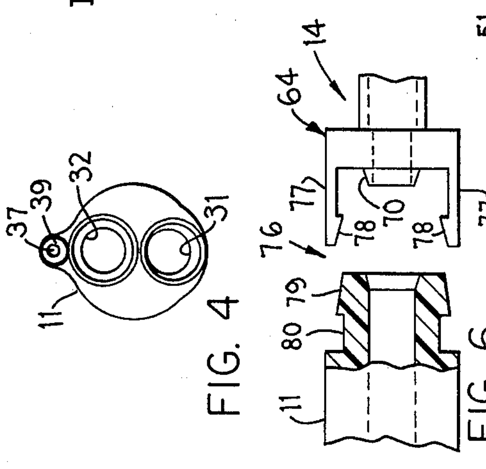
FIG. 4
FIG. 5
FIG. 6

59
58

54
57
56
60

IRRIGATION AND SUCTION HANDPIECE

FIELD OF THE INVENTION

This invention relates to an irrigation-suction handpiece for selectively applying an irrigant fluid to and withdrawing by suction of unwanted fluent material from, a dental or surgical operating site.

BACKGROUND OF THE INVENTION

Hand-held irrigation-suction devices have long been used in surgical and dental procedures for various purposes at the operating site, or wound, including flushing of debris from the operating site and clearing the site, by suction, of debris, excess irrigant fluid, blood, and other unwanted flowable material.

A typical prior suction-irrigator handpiece is disclosed in U.S. Pat. No. 3,889,675. Such prior handpiece includes a handle with irrigant fluid and suction passageways extending therethrough and mounts a detachable pair of working tips at its operating end, communicating with and continuing the irrigant and suction passageways of the handle. At the supply end of the handle, the passageways are connectible to suitable irrigant fluid and vacuum sources, through flexible conduits. To permit the operator (e.g., surgeon or dentist or assistant thereto) to achieve some degree of control of flow in the irrigant and suction passages, the handpiece is provided with a relief opening through the wall of the suction passage, which relief hole can be opened or closed by the index finger of the operator to vary the suction at the suction tip. In other words, with the hole open, the vacuum source draws through the hole as well as the tip and air leaking through the hole into the suction passageway necessarily reduces the suction strength, and hence material removal capability at the suction tip, opening of the hole, in effect "short circuiting" or substantially shutting off the suction at the tip.

On the other hand, the need to shut off the irrigant flow to the tip at the handpiece has, in the aforementioned prior art device, required incorporation of a manually actuable irrigant fluid valve in the irrigant fluid passageway in the handpiece, which substantially increases the structural complexity of the handpiece, the cost of the handpiece and, where the handpiece is to be reused, the difficulty of cleaning and sterilizing same. These difficulties particularly appear where the irrigant flow control valve in the handle is not only responsible for portioning of flow in the limited portion of the range of flow rates available, but is also to be responsible for a complete shut-off of irrigant fluid flow to the tip.

A further difficulty arises where, as in the aforementioned patented structure, the same irrigant valve is structure to handle both proportioning and complete shut-off of irrigant flow. Such a valve typically requires progressively increasing movement and pressure by the operator on the valve actuator to progressively open the valve against a resilient closing element. Whereas the operator may wish to merely select between two conditions, namely no irrigant flow and one irrigant flow rate intermediate the range of flow rates available through the valve, he nevertheless must maintain just the right finger pressure and displacement on the valve to effect that desired flow rate and any inadvertent operator change in finger pressure and position will result in an unwanted change in irrigant flow rate. Accordingly, the operator is required to devote to the irrigant flow valve an unnecessarily large portion of his attention, which could otherwise be directed to the dental or surgical procedure which he is performing or assisting.

Accordingly, the objects of this invention include provision of:

An irrigation-suction handpiece assembly for dental and surgical use at an operating site, which includes a handle having reduced complexity, cost and increased ease in cleaning and sterilizing.

A handpiece assembly, as aforesaid, having a handle free of manual irrigant flow valves, but which permits one-handed supporting of the handle, and shutting off or turning on of irrigant flow through the handpiece, and selection between full or reduced suction.

A handpiece assembly, as aforesaid, providing for location of an irrigant flow shut-off valve either adjacent or remote from the handle and further providing for remote air control of said valve by the hand of the operator as it grasps the handle.

Other objects and purposes of this invention will be apparent to persons acquainted with apparatus of this general type upon reading the following specification and inspecting the accompanying drawings.

SUMMARY OF THE INVENTION

The objects and purposes of the invention are met by providing an irrigation-suction handpiece assembly, for dental and surgical use at an operating site, including a handle containing longitudinally extending, side-by-side suction and irrigant passageways respectively connectible to a source of subatmospheric pressure and an irrigant fluid source. An irrigant valve is actuable for alternately opening and blocking flow of irrigant fluid from the source thereof through the irrigant passageway. An air pressure conduit includes a third passageway in the handle and connectible to an air pressure source which is not at atmospheric pressure and not influenced by pressure changes in the suction passageway. The third passageway has a portion in the handle selectively operable by the hand of the operator for effecting a change in the pressure within the third passageway. The irrigant valve has a control input coupled with the air pressure conduit and third passageway and responsive to such change in air pressure therein for shifting between its open and blocking states, to thereby control the flow of irrigant fluid to the operating site.

BRIEF DESCRIPTION OF THE DRAWINGS

FIG. 1 is a schematic side view of an irrigation-suction handpiece assembly including a handle and an irrigant flow control valve controllable from the handle.

FIG. 2 is an enlarged top view of the handpiece assembly of FIG. 1.

FIG. 3 is a central cross-sectional view substantially taken on the line III—III of FIG. 2.

FIG. 4 is a supply end view of the handle of FIG. 3.

FIG. 5 is a fragmentary exploded side view showing a snap-fit connection usable to interconnect the handle and tip assembly of FIG. 3.

FIG. 6 is a sectional view substantially taken on the line VI—VI of FIG. 5.

Figure 7:
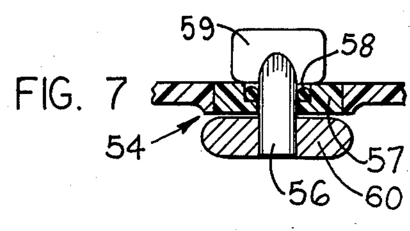
FIG. 7 is an enlarged fragment of FIG. 3 at the irrigant throttle valve.

Certain terminology will be used in the following description for convenience only and will not be limiting. The terms "forward" or "front end" and "operating end" will refer to the rightward end of the apparatus in FIGS. 1 and 3. The terms "supply end" or "rearward end" will refer to the left end of the apparatus in FIGS. 1 and 3.

DETAILED DESCRIPTION

An irrigation-suction handpiece 10, embodying the invention, includes a control handle 11 which at its rightward end 12 supports a removable tip assembly 14. Connected to the leftward, or supply, end 16 of the handle 11 are an irrigant supply conduit 18, a suction conduit 19 and a gas pressure conduit 20. For use such conduits 18, 19 and 20 are respectively connected to a source 22 of irrigant liquid (such as a pump) and a vacuum (i.e., subatmospheric pressure) source 23, and a gas pressure source 24. A valve 26 is interposed in the irrigant conduit 18 for opening or blocking irrigant flow from the source 22 through the handle 11. The valve 26 has a control input 27 responsive to the pressure in gas pressure conduit 20 as discussed hereafter.

In the preferred embodiment shown, gas pressure source 24 is a source of compressed gas, i.e., at above atmospheric pressure. For convenience, the following description refers to the gas as air though it will be understood that other gases, particularly nitrogen, may be employed.

It is also contemplated that the gas pressure source 24 may be a source of subatmospheric pressure, i.e. a suction or vacuum source. In the latter instance, sources 23 and 24 are either entirely separate vacuum sources or are sufficiently isolated, by any conventional means, that variations in pressure in suction conduit 19 during use of the handpiece 10 do not change the pressure in conduit 20 and valve control inlet 27. The valve 26 may be of any conventional type capable of alternately permitting, and completely blocking, irrigant flow therethrough in response to a preselected change in pressure at its control inlet 27. In the particular embodiment shown in FIG. 1, the valve 26 is schematically illustrated as a flexible tube clamp having a spring urged piston 28, responsive to superatmospheric pressure at control input 27 for driving such piston 28 against its spring to open the valve. A drop of pressure at control input 27, down to near atmospheric pressure, permits spring return of clamping piston 28 to its clamping, tube closed position shown.

Sources 22, 23 and 24 may be of any conventional type and normally will be remote from the handle 11 and the operating site. It is contemplated that the handle 11 may be structured to house the valve 26 and its control inlet 27 therein. However, it is preferred that the valve 26 be located remote from the handle 11, for example to keep any electrical components at a distance from the operating site, and to minimize the weight, bulk, complexity and cost of the handle 11. Conduits 18, 19 and 20 are flexible and preferably are conventional clear plastic tubing, for example of polyvinyl chloride.

While the sources 22, 23 and 24 may be of any conventional nature, such as pumps capable of supplying the desired pressure in conduits 19 and 20 and a pump or gravity flow system for supplying conduit 18, sources 22, 23 and 24, together with valve 26, are advantageously provided as parts of a remote control unit, schematically indicated by the broken line box 29, to which the supply ends of conduits 18, 19 and 20 preferably releasably connect. A preferred control unit is shown in copending U.S. application Ser. No. 79,869, assigned to the assignee of the present invention, and the disclosure of which is incorporated by reference herein.

In more detail, the handle 11, as seen in FIG. 3, is a unitary hollow body, preferably of rigid molded plastics material such as polystyrene. Preferably parallel irrigant and suction passageways 31 and 32 extend lengthwise through the handle 11 for connection at their supply ends to respective conduits 18 and 19 and for connection at their operating ends to tubular tips 34 and 35, respectively, of the tip assembly 14. In the preferred embodiment shown, suction passageway 32 is located above irrigant passageway 31.

A third passageway 37 (FIG. 3) extends rightward from the handle supply end 16 and terminated intermediate the ends of the handle in a control opening 38. In the preferred embodiment shown, the third passageway 37 extends substantially parallel to and above suction passageway 32 within a raised bead 39. The forward end 41 of the bead 39 is sloped rearward and upward at an angle of about 135 degrees from the forward extending top surface 42 of handle 11 and contains control opening 38, such that the passageway 37 opens forwardly through the sloped bead end surface 41.

Spaced forward of control opening 38 is a further control opening 45 which vents the suction passageway 32 to the atmosphere. Control openings 38 and 45 are spaced, but are close enough together as to allow the operator's finger, or thumb, to selectively close one or the other, or both of such control openings 38 and 45.

The passageways 31, 32 and 37 have enlarged diameter, rearwardly opening recesses 47, 48 and 49, respectively, for receiving snugly therein the opposed ends of flexible conduits 18, 19 and 20. To facilitate insertion of the conduit ends into the respective recesses, the open ends of the latter are angularly flared, as for example at 51. To minimize the height, and hence the bulk, of handle 11, the rear end portion thereof is extended downward at 54 and the recess 49 is offset downward from coaxial relation with passageway 31. The forward ends of the conduits 18, 19 and 20 fit snugly into the corresponding recesses 47, 48 and 49 and fixed therein in a leakproof manner. In the embodiment shown, the conduits are permanently affixed within the corresponding recesses as by adhesive bonding, although releasable connections, not shown, are contemplated.

An irrigant throttle valve 54 here comprises a stem 56 extending rotatably through a seat insert 57 fixed in the peripheral wall of passageway 31 and sealed against leakage of irrigant therepast by an O-ring 58 seated in a recess in insert 57. An irrigant throttle plate 59 is fixed to the inner end of stem 56 and thereby is rotatable to unblock or partially block passageway 31. The area of throttle plate 59 is preferably less than the cross sectional area of passageway 31 so as not to completely block the latter. A handle 60 is fixed to the outer end of stem 56 and is manually rotatable to adjust the throttle plate 59 and so adjust the rate of irrigant flowing through passageway 31 when the valve 26 is open.

The tip assembly 14 is removable to enable a variety of different tip assemblies to be used with the same handle 11. The hollow tubular tips 34 and 35 of different tip assemblies may vary substantially in configuration and material, to suit the needs of the particular dental or surgical procedure with which the handpiece assembly 10 is to be used. The tips 34 and 35 may be of any desired material, such as stainless steel or a suitable plastic material such as polycarbonate.

The tip assembly 14 includes an end cap 64 to which the left, or rear ends of tips 34 and 35 are affixed. In the embodiment shown, the end cap 64 is of a rigid plastic material, such as polystyrene. The rear end portions of the tips 34 and 35 are fixed as by adhesive bonding in recesses 65 and 66 in end cap 64, and communicate through corresponding openings 67 and 68 in the end cap with the passages 32 and 31, respectively, of handle 11.

The end cap 64 is fixed to the forward end of handle 11 in a sealed manner to avoid leakage of irrigant fluid or air and fluid waste products flowing between the tips and handle. More particularly, noses 70 and 71 protrude rearwardly from the end cap 64 into the forward ends of the handle passageways 32 and 31 and contain the openings 67 and 68. In the embodiment shown, the nose 70 is tapered and is wedged snugly into a correspondingly tapered relief at the forward end of suction passageway 32. The other nose 71 is stepped to coaxially receive an O-ring 72 which bears in liquid sealing relation against a recessed cylindrical surface at the forward end of irrigant passageway 31.

The tip assembly 14 is fixed to the handle 11 in the preferred embodiment shown by a snap-fit connection 76 (FIGS. 5 and 6). The snap-fit connection includes an opposed pair of generally parallel, rearwardly extending, elastically bendable fingers 77, provided at their rearward ends with inwardly disposed, rearwardly tapering teeth 78. The forward end of the handle 11 has sidewalls incorporating a pair of ramps 79 diverging rearwardly to an oppositely facing pair of undercut grooves 80. Thus, upon rearward movement of the tip assembly 14 toward the handle 11 the ramps 79 spread the toothed ends 78 of fingers 77, whereafter the teeth 78 drop into the grooves 80 and lock the top assembly 14 snugly and sealingly to handle 11, with noses 70 and 71 protruding into the handle passageways as above discussed with respect to FIG. 3.

The top and bottom ends of at least the undercut grooves 80 are overhung by shoulders 81 which prevent vertical shifting or pivoting of the teeth 78 on the handle 11 and thereby assist the noses 70 and 71 in securing the tip assembly 14 rigidly to the handle 11.

The fingers 77 of end cap 64 may be gripped and bent resiliently outward to permit axial separation of the tip assembly 14 from the handle 11.

OPERATION

While the operation of the disclosed apparatus will be apparent from the foregoing description thereof, same is summarized below.

With the desired tip assembly 14 installed in the front end of handle 11, as above discussed with respect to FIGS. 3, 5 and 6, and tip assembly 14, handle 11 and conduits 18, 19 and 20, extending from the handle in sterile condition, the leftward ends (FIG. 1) of flexible conduits 18, 19 and 20 can then be connected to irrigant valve 28 and the irrigant liquid, vacuum and air pressure sources 22, 23 and 24, in the manner discussed above as to FIG. 1. Such connections are conveniently made by connection of conduits 18, 19 and 20 to the control unit, indicated in broken lines at 29, or as disclosed in aforementioned U.S. application Ser. No. 79,869.

With sources 22, 23 and 24 energized, and holes 45 and 38 in their normally uncovered condition, little or no suction is present at the forward end of suction tip 35 and no irrigant liquid flows through the handle 11 and irrigant tip 34.

Tip suction and irrigant flow from the irrigant tip can be provided individually or simultaneously. More particularly, with the handle 11 held in the hand H (FIG 1) of the operator, the operator may conveniently cover the hold 45 with his thumb or finger. This eliminates the bleed of air through hole 45 into suction passageway 32, such that the full suction, generated at the handpiece by the remote vacuum source 23, appears at the open forward end of suction tip 35, for removing fluent materials from the operating site.

On the other hand, the operator's thumb or finger can be used to close hole 38 (instead of or simultaneously with its covering of hole 45). When open, the hole 38 acts as a relief for passageway 37, conduit 20 and valve control inlet 27, tending to keep same at near atmospheric pressure. On the other hand, closing of hole 38 causes passageway 37, conduit 20 and valve control inlet 27 to change pressure, to the pressure of air pressure source 24. This change in pressure at control inlet 27 opens the irrigation valve 26 producing a flow of irrigant liquid from source 22 through conduit 18, passageway 31 and out the front end of irrigant tip 34 to the operating site. In the embodiment shown, the air pressure source 24 is at above atmospheric pressure (i.e., a compressed air source) and the valve 26 responds to superatmospheric pressure at its control inlet 27 by staying open. However, it is also contemplated that air pressure source 24 may be a subatmospheric source (i.e., vacuum source), the valve 26 in that instance being a conventional valve which opens in response to a change from substantially atmospheric to subatmospheric pressure of the source.

In the preferred embodiment of the control system a pilot operated valve (not shown) may be interposed in the line 27 to allow the operation of gas line 20 at a lower pressure than required to unblock the valve 26, the pressure in line 20 being used to control the pilot of said pilot operated valve to cause same to actuate valve 26 from a conventional high pressure source, not shown.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. In an irrigation-suction tool incorporating an air pressure conduit connectible to an air pressure source, a suction conduit connectible to a suction source and an irrigant liquid conduit connectible to an irrigant liquid source, a valve interposed in said irrigant liquid conduit and normally biased to block irrigant liquid flow through said irrigant liquid conduit, said valve having a control portion connected to said air pressure conduit and responsive to change in air pressure past a threshold in said air pressure conduit for causing said valve to open said irrigant liquid conduit to flow therethrough and responsive to a reverse change in air pressure past said threshold for permitting said valve to return to its flow-blocking condition thereby shutting off irrigant liquid flow through said irrigant liquid conduit, a tip unit having a forward end placeable adjacent the operating site, said tip unit comprising hollow elongate suction and irrigant liquid tips for respectively removing liquid materials from the operating site and supplying irrigant liquid thereto;

the improvement comprising:

a handle in the form of an elongate rigid body of plastics material containing three elongate parallel passageways formed integrally in said body in vertically stacked relationship isolated from each other, said passageways including an irrigant liquid passageway and a suction passageway extending longitudinally between and opening through the front and rear ends of said body, said irrigant liquid and suction passageways extending longitudinally of said body with said irrigant liquid passage extending along the bottom wall of said body and said suction passage extending along the upper wall of said body, a bead extending longitudinally along the top of said body from the rear end of said body to near the longitudinal central portion of said body, an air pressure passage extending longitudinally through said bead above said suction passage, said bead being of substantially smaller cross sectional area than the remainder of said body, said air pressure passage opening forwardly through the forward end of said bead above said suction passage and forming an air pressure control port, an opening through the top wall of said body into said suction passage and forming a suction control port, said suction control port being spaced forward of and adjacent said air pressure control port at a distance permitting both alternate and simultaneous closure of said ports by the thumb or finger of the operator's hand carrying the body, said body having means at the rear end thereof for connecting said rear ends of said passages to corresponding ones of said air pressure, suction and irrigant liquid conduits for simultaneous control of flow of irrigant liquid and suction by a single finger of the hand carrying the body without need for valves in or near the body or cross connections of said passages in or near said body, said body having means for connecting said tips to the forward end thereof, said tip unit being free of connection to said air pressure conduit, the portion of said tool forward of said air pressure control port being free of any portions of said air pressure passageway, said means for connecting said body to said tips and conduits being of releasable type to facilitate cleaning of said body by disconnection from said conduits and tips.

2. The apparatus of claim 1, in which the front end surface of said bead slopes downwardly and forwardly to the upper wall of said body, said air pressure control port being in said sloped forward wall and normally providing a forward flow of pressurized air from said air pressure conduit, said suction control port facing upward toward the airstream from said air pressure control port which passes thereabove.

3. The apparatus of claim 1, including a throttle unit rotatably supported on said body and having a shank extending through the bottom wall of said body into said irrigant liquid passageway and supporting a throttle plate therein, said throttle plate being sized at less than cross-sectional area of said irrigant liquid passageway and being rotatable between partially blocking and substantially nonblocking positions, said throttle valve having a handle fixed to said shank outside said body.

4. The apparatus of claim 1, in which said body is a monolithic member, said handle including a substantiallyrigid end cap fitted on the forward end of said handle and having the rear ends of said hollow tips bonded thereto in communication therethrough with said suction and irrigant liquid passageways in said handle, a releasable snap fit connection means for releasably fixing said cap on said handle, said snap fit connection means including a pair of laterally opposed, inwardly toothed, outwardly flexible blades extending rearward from said end cap, said blades being spaced on opposite sides of said tips, said tips being vertically stacked in a zone extending between said pair of blades, said body having sidewardly facing undercut channels on opposite sides thereof for receiving the internally toothed ends of said blades in snap-fit relation therein to securely hold said end cap to the forward end of said body, said body end and end cap being respectively provided with complementary conical tips and recesses coaxial with the corresponding tips, said blades being of height less than the height of said body, said body having laterally extending shoulders overhanging at least the undercut parts of the channels receiving the toothed inner ends of said blades for snugly gripping the upper and lower edges of said blades therebetween and thereby preventing vertical shifting or pivoting of the end cap on the body end and thereby assisting the coacting conical portions of said end cap and body in sealingly connecting said suction and liquid passageway in said body to corresponding said tips.

5. An irrigation-suction handpiece assembly for dental and surgical use at an operating site, including:

a monolithic, elongate handle having longitudinal through passageways for irrigant liquid and suction, respectively, said suction passageway being adjacent one side of said handle and a bleed hole communicating through said one side of said handle with said suction passageway in the central longitudinal portion of said handle, a bead extending along said one side of said handle from the rear end of said handle toward said suction bleed hole and stopping short thereof in close spaced relation thereto, said bead having an air pressure passageway extending longitudinally therethrough from the rear end of said handle and opening through the forward end thereof in an air pressure bleed hole adjacent said suction bleed hole, conduits respectively connecting said air pressure passageway and suction passageway and irrigant liquid passageway to corresponding air pressure, suction and irrigant liquid sources, and a normally blocking valve interposed in said irrigant liquid conduit remote from said handle and having a control input connected to said air pressure conduit, tubular tips extending from the forward end of said handle to be placed at an operating site, said handle being free of valves therein but providing direct control of suction force and irrigant flow by a finger of the hand carrying said handle alternately or simultaneously closing or opening said adjacent bleed holes in said handle.

* * * * *